United States Patent [19]

Kelsey, Jr. et al.

[11] 4,398,980

[45] Aug. 16, 1983

[54] METHOD FOR FABRICATING A SEAL BETWEEN A CERAMIC AND A METAL ALLOY

[76] Inventors: Paul V. Kelsey, Jr., Idaho Falls; William T. Siegel, Rigby, both of Id., granted to U.S. Department of Energy under the provisions of 42 U.S.C. 2182

[21] Appl. No.: 286,422

[22] Filed: Jul. 24, 1981

[51] Int. Cl.³ .................... C03B 29/00; C04B 33/34; B23K 31/02
[52] U.S. Cl. ........................ 156/89; 156/311; 156/322; 228/232; 228/903
[58] Field of Search ............ 156/89, 82, 81, 272, 156/273, 311, 309.9, 322; 428/469, 472; 228/200, 218, 219, 220, 230, 231, 232, 211, 902, 903, 227, 228, 239; 29/428, 722

[56] References Cited

U.S. PATENT DOCUMENTS

| | | | |
|---|---|---|---|
| 3,363,306 | 1/1968 | Kirkpatrick | 228/200 |
| 3,577,629 | 5/1971 | Watts et al. | 228/232 |
| 3,882,596 | 5/1975 | Kendziora | 228/232 |

*Primary Examiner*—Edward C. Kimlin
*Assistant Examiner*—Louis Falasco
*Attorney, Agent, or Firm*—Sandra B. Weiss; John M. Albrecht; Richard G. Besha

[57] ABSTRACT

A method of fabricating a seal between a ceramic and an alloy comprising the steps of prefiring the alloy in an atmosphere with a very low partial pressure of oxygen, firing the assembled alloy and ceramic in air, and gradually cooling the fired assembly to avoid the formation of thermal stress in the ceramic. The method forms a bond between the alloy and the ceramic capable of withstanding the environment of a pressurized water reactor and suitable for use in an electrical conductivity sensitive liquid level transducer.

8 Claims, No Drawings

METHOD FOR FABRICATING A SEAL BETWEEN A CERAMIC AND A METAL ALLOY

CONTRACTUAL ORIGIN OF THE INVENTION

The U.S. Government has rights in this invention pursuant to Contract No. DE-AC07-76IDO1570 between the U.S. Department of Energy and EG&G Idaho, Incorporated.

BACKGROUND OF THE INVENTION

This invention relates to a method of fabricating a strong seal between a ceramic and a metal alloy. More specifically, the invention relates to a method of fabricating a seal strong enough to withstand extreme conditions of temperature and pressure such as those found in the environment of a pressurized water reactor (PWR).

The use of pressurized water reactors has required the development of special instruments capable of withstanding severe steady state PWR conditions. Typical of these instruments is the liquid-level transducer, an instrument used to acquire data on transient, two-phase fluid behavior in a PWR. Each transducer is comprised in part of several electrodes. Each electrode comprises in part of coaxial center pin and outer housing, both made of an electrically conductive alloy and separated from one another by a coaxial ceramic sleeve. The ceramic sleeve terminates in a ceramic seal at the point at which the center pin extends beyond the housing. A constant current is passed through the center pin and the housing and the resulting voltage between the pin and housing is measured. When the electrode is immersed in water, the water provides a conduction path for the current so that the conductivity is high and the resulting voltage is low; conversely, when the pin is dry, the conductivity is low and the voltage is high. These transducers may be mounted at different levels on the interior of a reactor vessel to indicate the water level in the vessel. If water permeates the ceramic sleeve between the pin and the housing the voltage will always be low and the electrode will give erroneous results. Thus if the ceramic seal is defective, the electrode will fail.

Seals prepared by conventional methods have proven unsatisfactory for the harsh environment of a PWR. Seals are commonly prepared by prefiring the alloy in a reducing atmosphere such as the "burnt gas" atmosphere commonly used in the art. "Burnt gas" atmospheres are quite variable in composition; the partial pressure of oxygen generally ranges anywhere from over $10^5$ Pa to about 1 Pa. The prefired alloy and the ceramic are then hot-pressed and fired together in air. Under these conditions the formation of oxides on the surface of the alloy cannot be controlled, and oxides which are not conducive to bonding may grow. Seals produced in this manner often have voids in the ceramic and poor bonding between the alloy and the ceramic. These seals have failed under the high temperature and pressures characteristic of a PWR.

The poor bonding is a result of materials used in the manufacture of the electrode. The alloy used in the center pin and outer housing is typically Inconel X-750, which contains significant quantities of nickel, chromium, titanium, iron, cobalt, aluminum and silicon. By current methods, during the prefiring step the alloy forms a scale of $NiTiO_3$ on top of a layer of $NiCr_2O_4$. These oxides have incompatible thermal expansion characteristics, which lead to spalling along the oxide interface. Additional problems may arise during the firing step. Molten ceramic will form a strong bond with certain types of oxides, but if the molten ceramic dissolves the entire surface oxide on the alloy, the ceramic will come in direct contact with the alloy and only weak van der Waals bonds will be formed.

SUMMARY OF THE INVENTION

It is one object of the present invention to provide a method of fabricating a seal between a ceramic and a metal alloy.

It is another object of the present invention to provide a method of fabricating a seal between a ceramic and a metal alloy that can withstand the environment of a pressurized water reactor.

It is another object of the present invention to provide a method of fabricating a seal between a ceramic and a metal alloy suitable for use in an electrical conductivity sensitive liquid level transducer for use in a pressurized water reactor.

Additional objects, advantages, and novel features of the invention will be set forth in part in the following description.

In accordance with the invention, the method of fabrication comprises prefiring the metal alloy in an atmosphere with a very low oxygen partial pressure, cooling the alloy, placing the ceramic in contact with the alloy, quickly firing the ceramic and alloy in air to form a bond therebetween and carefully cooling the bonded ceramic and alloy to avoid thermal stresses on the newly formed bond. The prefiring of the alloy in an atmosphere with a very low oxygen partial pressure causes an oxide to form on the alloy surface which is stable and strongly bonded to the alloy. When the ceramic and alloy are fired together in air, the ceramic melts whereupon it dissolves a small amount of the surface oxide layer. This forms a strong bond between the ceramic and the oxide, providing a hermetic seal between the ceramic and the alloy.

A seal fabricated by the method of the subject invention is strong enough to withstand the severe temperatures and pressures characteristic of a pressurized water reactor. These seals may be used in the internal instrumentation for these reactors where ordinary ceramic-alloy seals would fail. The method is simple, reliable and inexpensive, and does not require any unusual apparatus.

DETAILED DESCRIPTION OF THE PREFERRED EMBODIMENT

The following is a detailed description of a preferred embodiment of the subject invention; other embodiments will be readily apparent to those skilled in the art.

By the method of the subject invention, the alloy parts for the electrodes are prefired in a strongly reducing atmosphere such as a mixture of $H_2$ and $CO_2$ at a temperature of about 1100° C. for about 1–3 hours. The partial pressure of oxygen should be less than or equal to $10^{-10}$ Pa and is preferably on the order of $10^{-14}$ Pa. The reducing atmosphere is maintained while the alloy parts are allowed to cool. After cooling the alloy parts and ceramic are assembled in the desired configuration and fired in air at a temperature of about 1050° C. for about 8 to 12 minutes. The firing in air must be done very quickly, so that the maximum temperature is reached in one to two minutes. An induction furnace is well-suited to this purpose. The temperature is quickly reduced to about 810° C. and maintained for about three minutes, then gradually reduced to about 540° C. and maintained for about 5 minutes. The induction furnace is then turned off and the alloy-ceramic assembly allowed to cool to room temperature before it is removed from the furnace.

The method of the subject invention forms an unusually strong seal between the alloy and the ceramic. When the alloy used is Inconel X-750, prefiring under the prescribed conditions produces a surface layer of the oxides $Al_2O_3$ and $Cr_2O_3$. These hexagonal oxides are slow to form and stable. They adhere strongly to the alloy surface, and will not crumble, flake, or peel off. The very low partial pressure of oxygen encourages the formation of $NiTiO_3$ which is also hexagonal and therefore has thermal expansion characteristics compatible with $Cr_2O_3$. This increases the adherence of the oxide layer to the substrate alloy forming a seal impervious to oxygen. A higher partial pressure of oxygen such as that used in prior art methods would lead to the formation $TiO_2$ and $NiCr_2O_4$ which are tetragonal and therefore not compatible with the surface of the prefired alloy. These oxides would spall off the alloy resulting in seal failure.

The quick firing of the assembled ceramic and alloy parts in air accomplishes several purposes. The ceramic becomes molten and dissolves a small amount of the oxide on the alloy surface forming a strong bond between the ceramic and the oxide layer. This in conjunction with the strong bond between the oxide and the substrate alloy forms a very strong bond between the ceramic and the alloy. The ceramic typically contains a large quantity of barium silicate and significant amounts of $As_2O_3$, $Bi_2O_3$, and other metallic oxides. The high partial pressure of oxygen during the quick-firing prevents the decomposition of the $As_2O_3$ and $Bi_2O_3$ to elemental arsenic and bismuth. These would form a metallic coating on the ceramic which would inhibit the dissolution of the surface oxide on the alloy. Inconel X-750 is also wetted best when the firing is done at high partial pressures of oxygen as indicated by reduced contact angles between the ceramic and the alloy measured during sessile drop experiments. The firing in air must be done quickly to avoid the formation of the tetragonal $TiO_2$ and $NiCr_2O_4$ in the alloy. Also, if the firing is too long, gas bubbles will form in the ceramic leading to voids and seal failure.

The cooling of the fired seal is carefully controlled to prevent thermal stresses in the ceramic. The portion of the cooling cycle wherein the seal is maintained at a temperature of about 810° C. is important because it relieves thermal stresses in the ceramic while avoiding the formation of tetragonal oxides in the alloy.

EXAMPLE

Unassembled Inconel X-750 components of the electrode were cleaned with acetone. A quartz tube was purged with argon, the Inconel X-750 components were loaded in the tube, and the tube was purged with a reducing atmosphere of 99.9% $H_2$ and 0.1% $CO_2$. By this method an oxygen partial pressure of about $10^{-14}$ Pa was attained. The reducing atmosphere was maintained throughout the prefiring of the alloy components. The tube containing the alloy components was heated in a furnace at $1100° \pm 5°$ C. for 3 hours. The tube was gradually cooled and purged with argon for at least 15 minutes. The prefired components were washed in acetone.

The prefired components and ceramic beads were assembled in the desired configuration. The assembly was placed in a pyrex tube and the tube loaded in an induction furnace. The furnace was brought from ambient temperature to $1050° \pm 5°$ C. in less than 2 minutes and held at that temperature for 10 minutes. The temperature was lowered to $810° \pm 5°$ C. over a period of 90 seconds and held for 3 minutes. The temperature was then lowered to $540° \pm 5°$ C. over a period of 6 minutes and held for 5 minutes. The furnace was then allowed to cool to room temperature.

The resulting ceramic-alloy seal was stable at a water pressure of $2.4 \times 10^7$ Pa for 30 minutes, and at a water pressure of $1.5 \times 10^7$ Pa and a temperature of 343° C. for 24 hours. These same conditions would cause failure in seals made by prior art methods.

The foregoing description of a preferred embodiment is not intended to limit the invention to the precise form disclosed. Obviously, many modifications and variations are possible in light of the above teaching. The embodiment was chosen and described in order to best explain the principles of the invention and its practical application.

What is claimed is:

1. A method of fabricating a seal between a ceramic and a metal alloy comprising:
    prefiring the alloy in a reducing atmosphere with an oxygen partial pressure less than or equal to $10^{-10}$ Pa,
    cooling the alloy in said reducing atmosphere,
    placing the ceramic in contact with the alloy,
    firing the ceramic and alloy in air, and
    cooling the ceramic and alloy to a temperature below a firing temperature but above ambient temperature, holding at said temperature for a set period of time, then cooling to ambient temperature whereby a seal is formed therebetween.

2. The method of claim 1 wherein the prefiring of the alloy is done in an atmosphere with an oxygen partial pressure of less than $10^{-14}$ Pa.

3. The method of claim 1 wherein the prfiring of the alloy is of a duration of 1 to 4 hours.

4. The method of claim 3 wherein the prefiring of the alloy is carried out at a temperature between 950°–1150° C.

5. The method of claim 1 wherein the firing of the ceramic and alloy in air is of a duration of 5 to 30 minutes.

6. The method of claim 5 wherein the firing of the ceramic and alloy is carried out at a temperature between 950°–1150° C.

7. The method of claim 6 wherein the firing of the ceramic and alloy is carried out so that the temperature of the ceramic and alloy rises from ambient temperature to about 1050° C. in less than 2 minutes.

8. The method of claim 1 wherein the fired ceramic and alloy are cooled from firing temperature to about 800° C. and are held at about 800° C. for about three minutes before cooling to ambient temperature.

* * * * *